(12) United States Patent
Oktay

(10) Patent No.: US 7,097,658 B2
(45) Date of Patent: Aug. 29, 2006

(54) FLEXIBLE MEMS ACTUATED CONTROLLED EXPANSION STENT

(76) Inventor: Hasan Semih Oktay, 620 Lions Gate La., Odenton, MD (US) 21113

( * ) Notice: Subject to any disclaimer, the term of this patent is extended or adjusted under 35 U.S.C. 154(b) by 85 days.

(21) Appl. No.: 10/226,706

(22) Filed: Aug. 22, 2002

(65) Prior Publication Data

US 2003/0040791 A1 Feb. 27, 2003

(51) Int. Cl.
*A61F 2/82* (2006.01)
(52) U.S. Cl. ...................... 623/1.2; 623/1.15
(58) Field of Classification Search .............. 623/1.11, 623/1.12, 1.15, 1.18, 1.2; 606/191, 192, 606/194, 198; 128/899
See application file for complete search history.

(56) References Cited

U.S. PATENT DOCUMENTS

| | | | | |
|---|---|---|---|---|
| 5,776,181 A | * | 7/1998 | Lee et al. .................. | 623/1.15 |
| 5,972,029 A | * | 10/1999 | Fuisz ......................... | 623/1.2 |
| 6,053,873 A | * | 4/2000 | Govari et al. ............... | 606/191 |
| 6,139,573 A | * | 10/2000 | Sogard et al. ............... | 623/1.3 |

* cited by examiner

*Primary Examiner*—Brian E. Pellegrino
(74) *Attorney, Agent, or Firm*—Stainbrook & Stainbrook, PC; Craig M. Stainbrook

(57) ABSTRACT

An automatically controlled expansion stent having an expansible stent body, actuation means for expanding the stent body, and control means for actively controlling the actuation means. The stent body is substantially tubular and includes material layers covering a plurality of radial expansion trusses. The stent employs MEMS motors under the control of a programmable logic device to expand the trusses and the stent body. Force from the motor is communicated to the expansion trusses through interconnects, which pivotally connect the trusses and provide channels for pull wires extending from the motors to the trusses. The trusses comprise a plurality of hinged links which produce symmetrical expansion of the stent body when actuated by the MEMS motor.

5 Claims, 14 Drawing Sheets

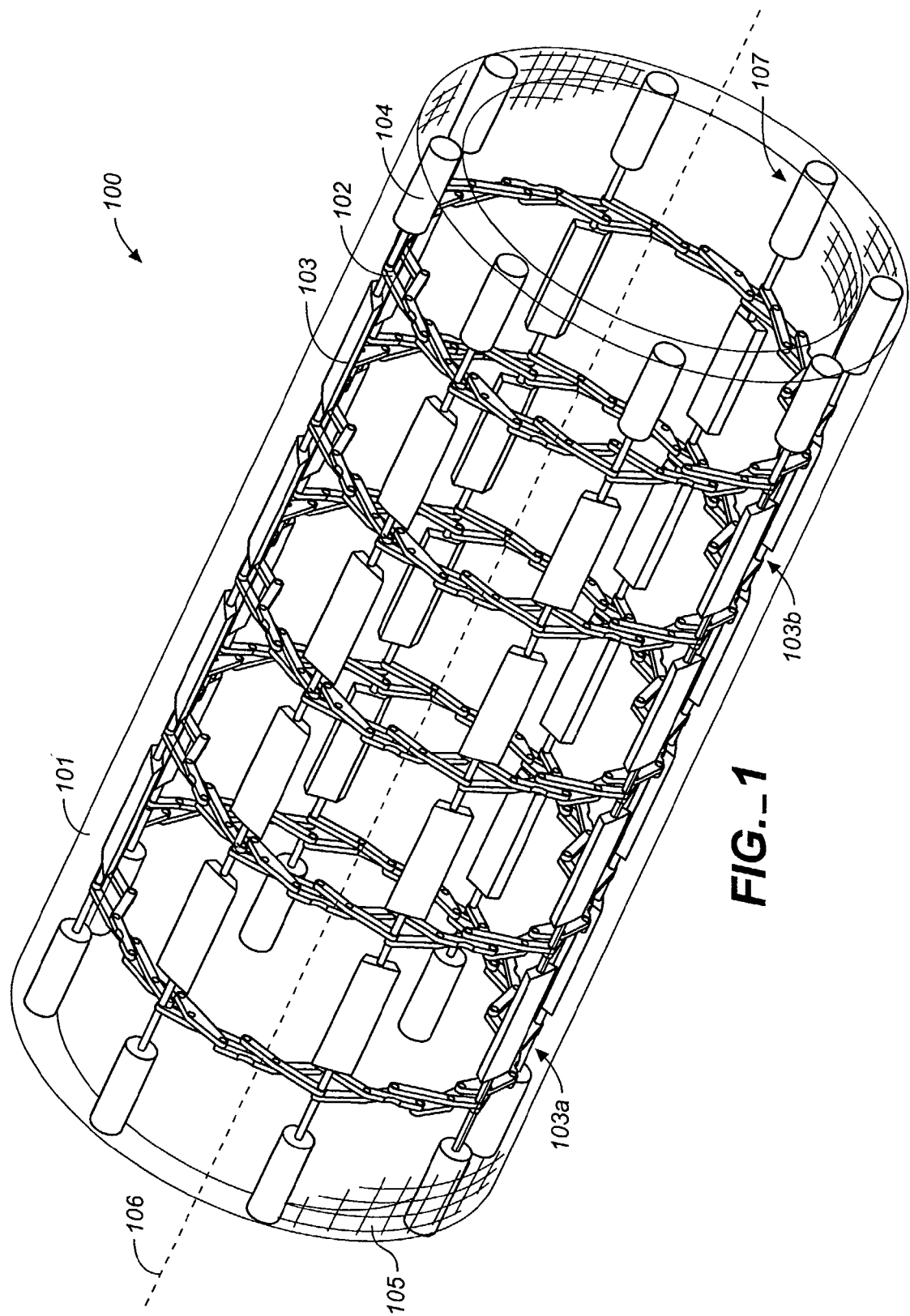
FIG._1

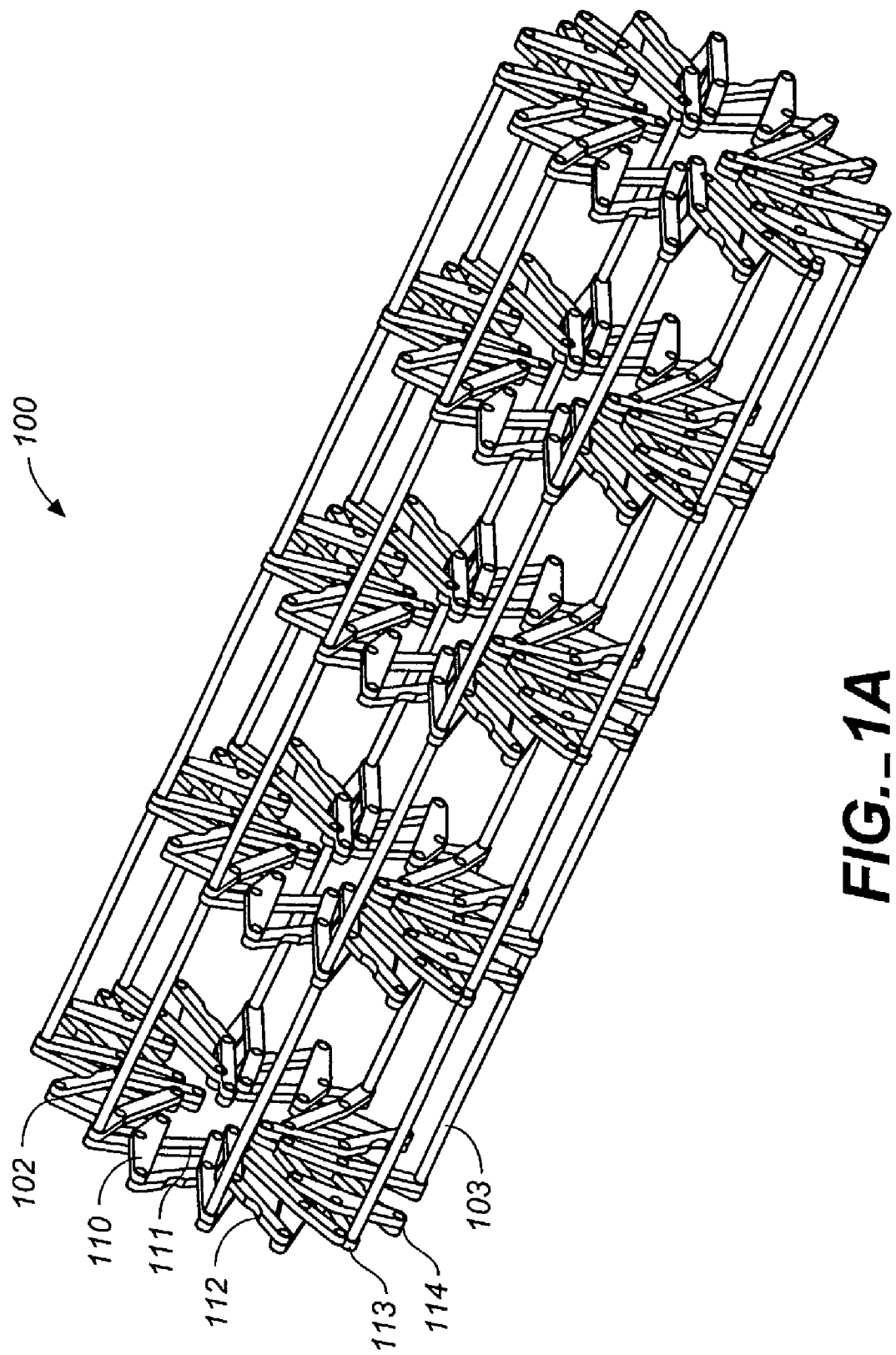
FIG._1A

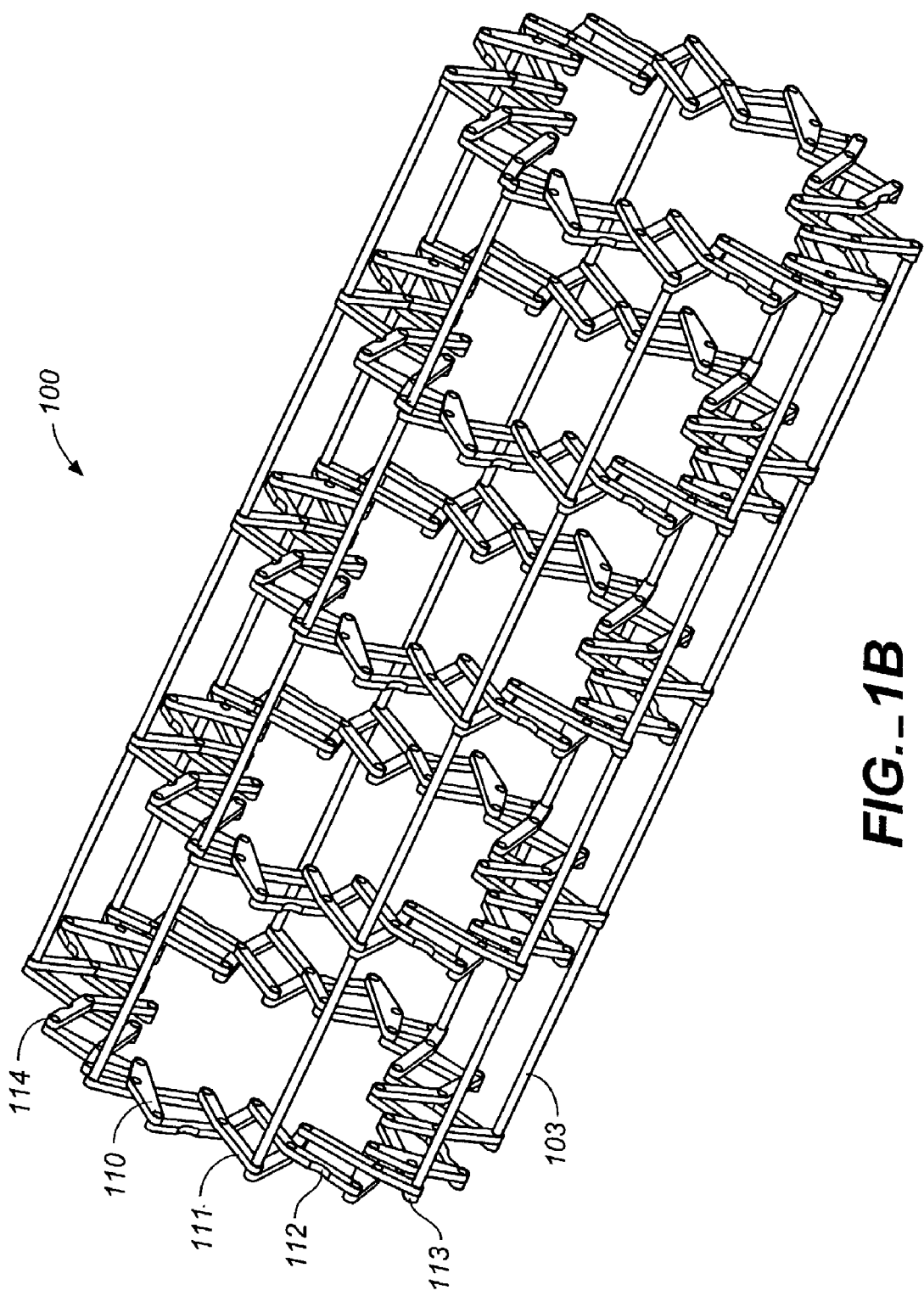
FIG._1B

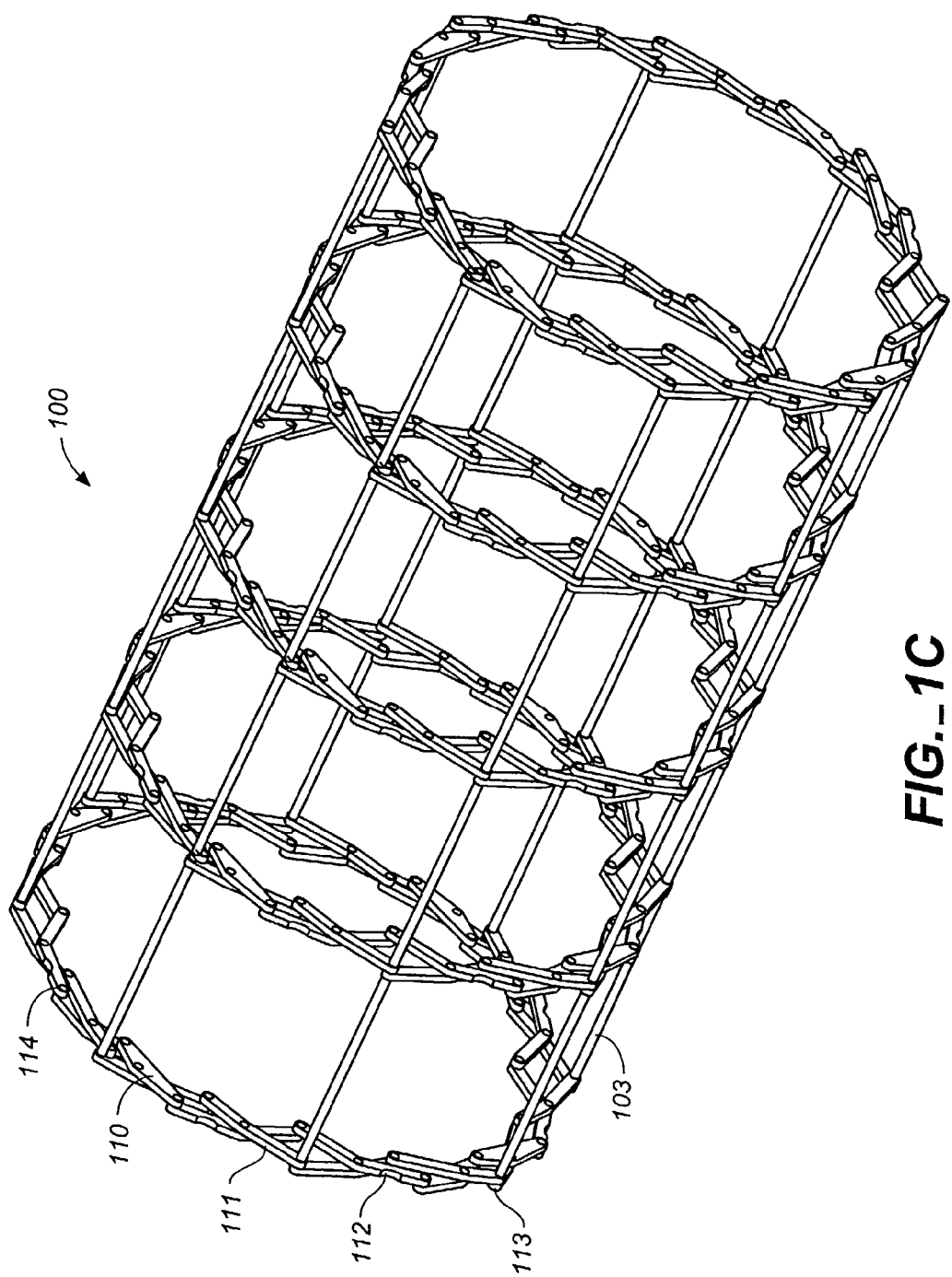
FIG._1C

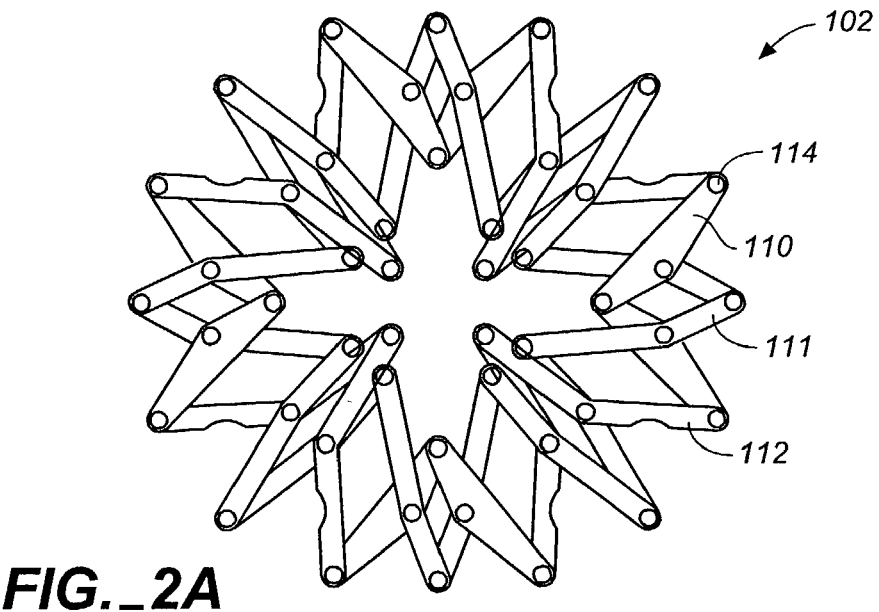
FIG._2A
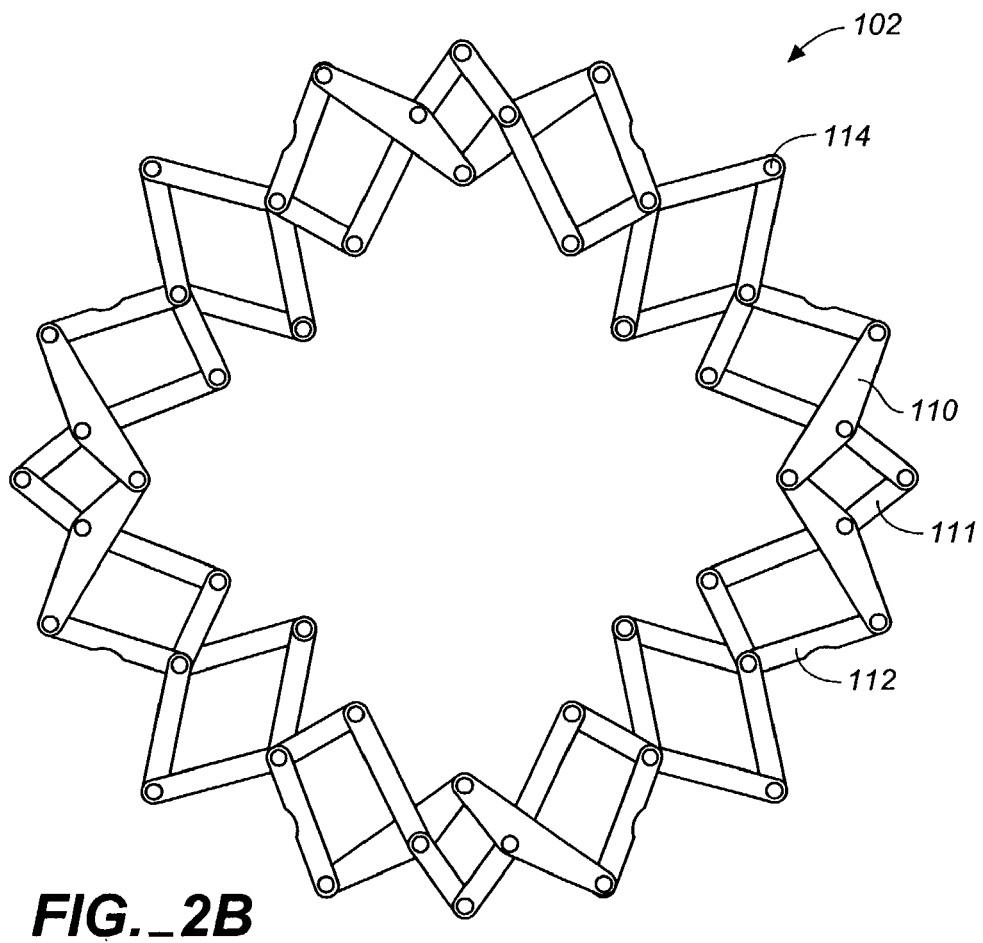
FIG._2B

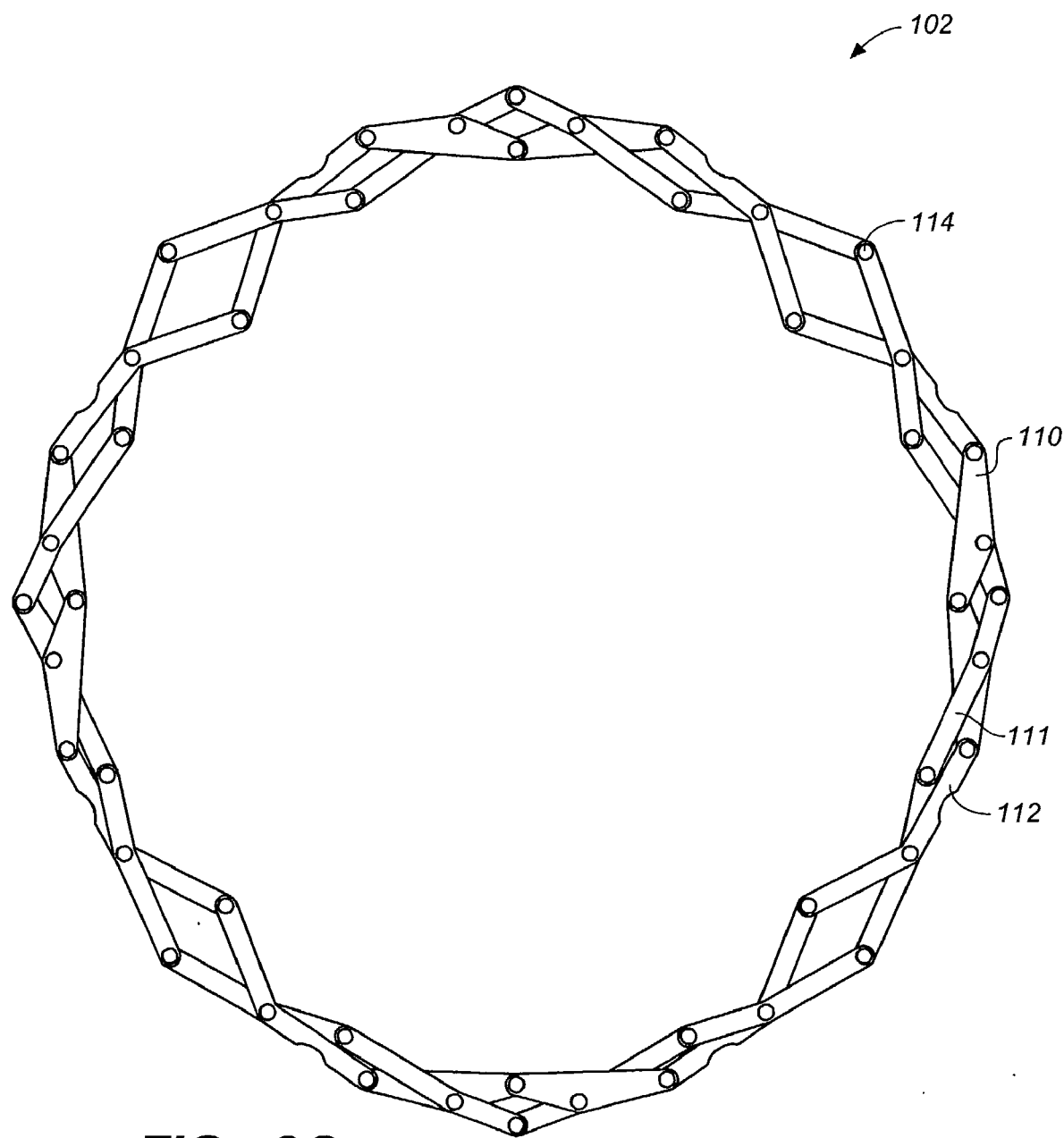
FIG._2C

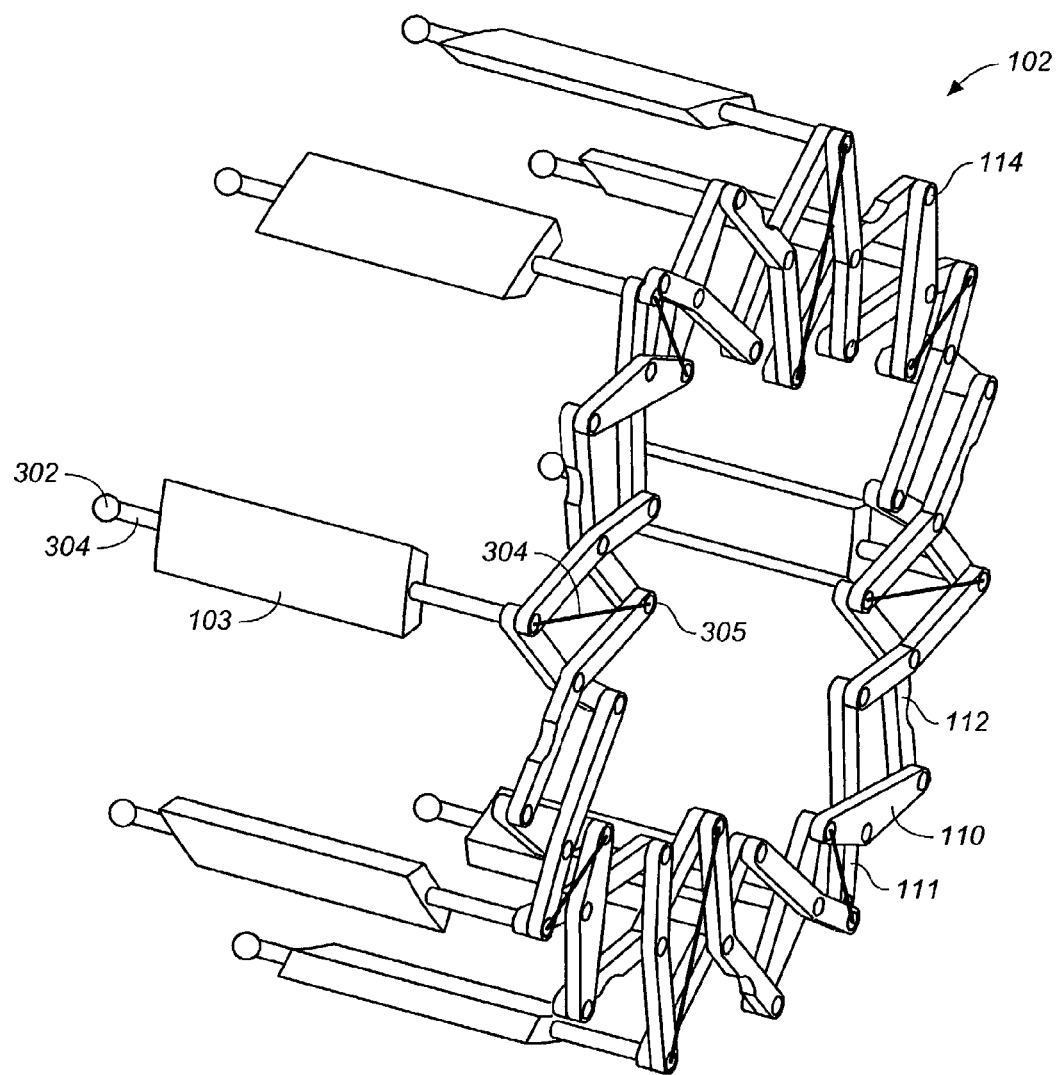
FIG._3

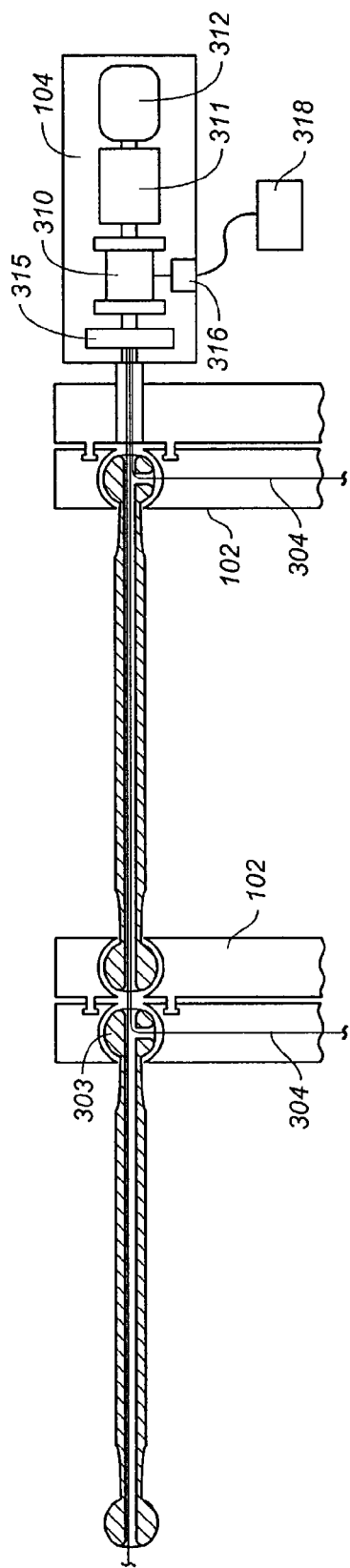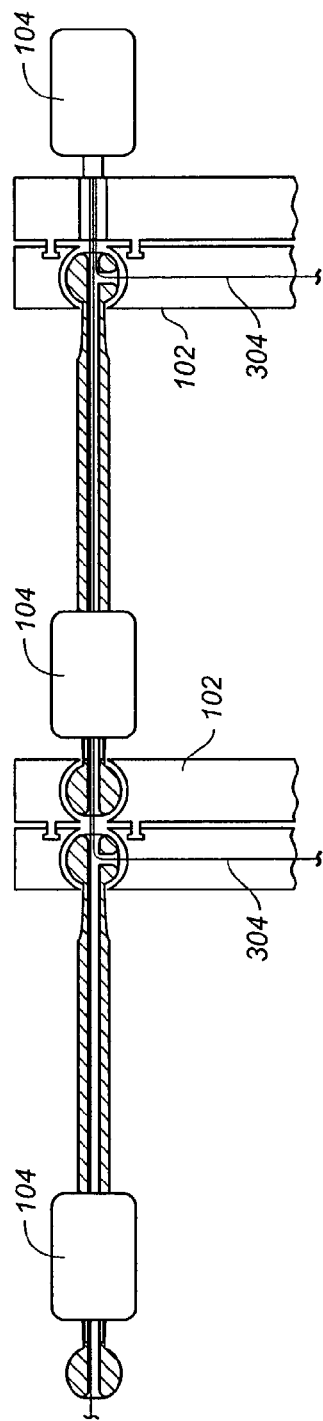

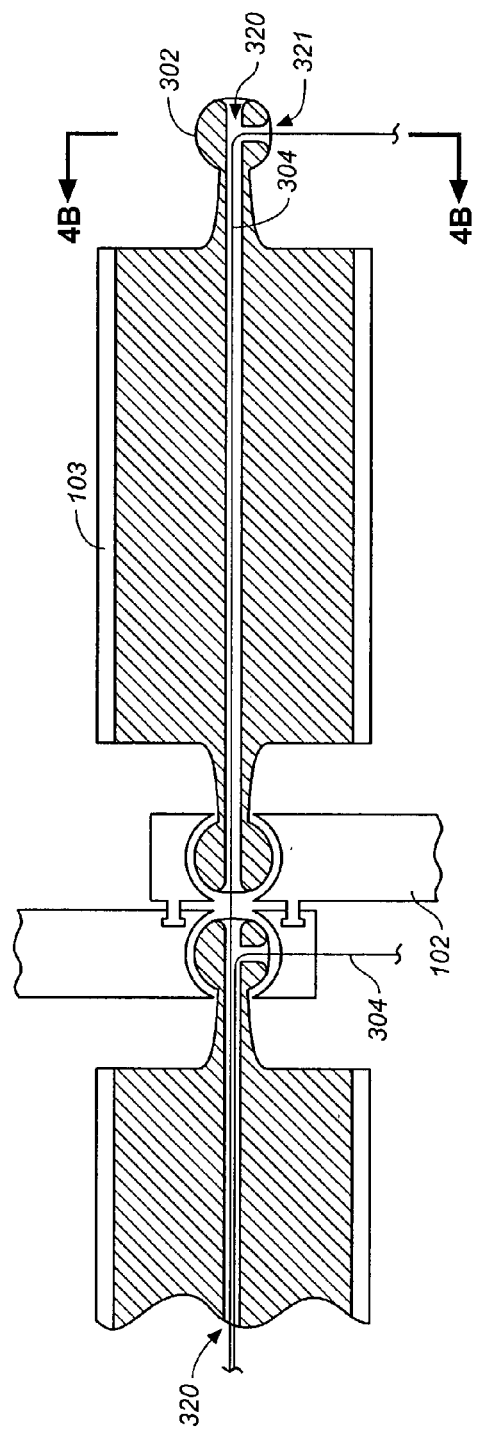
FIG._4A
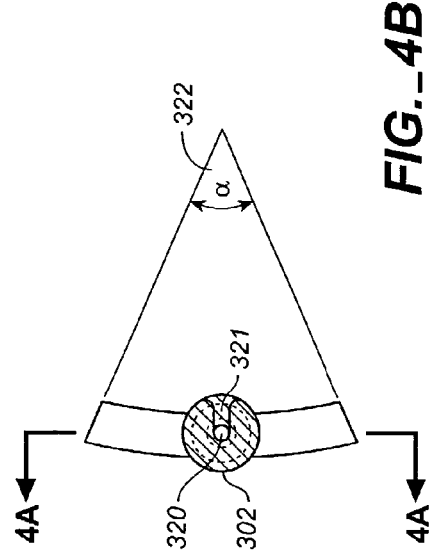
FIG._4B

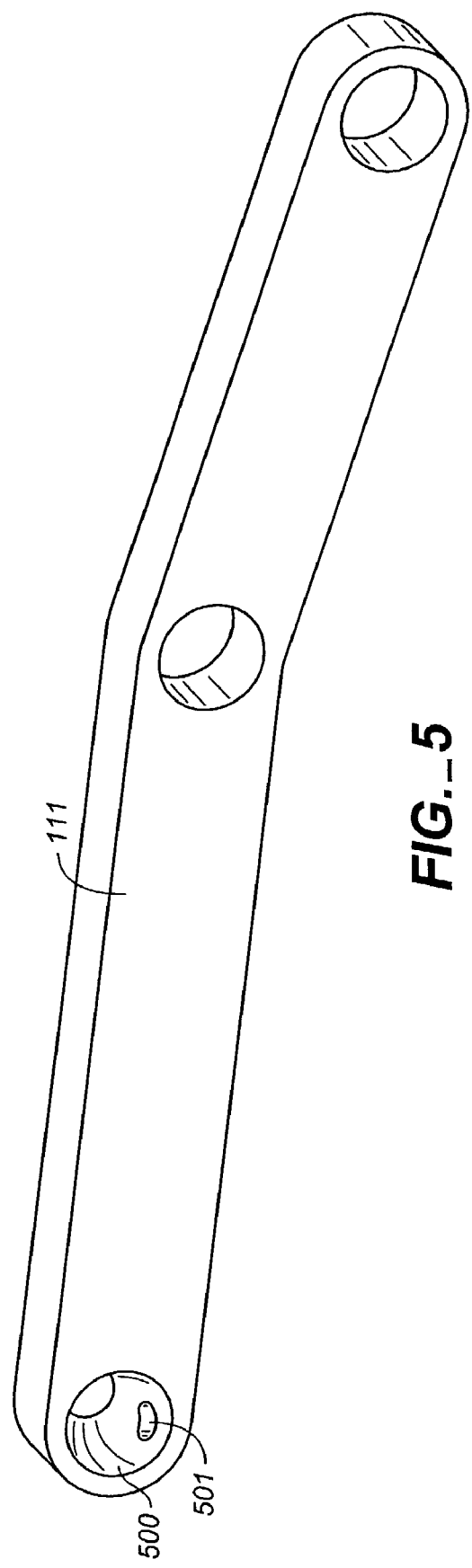

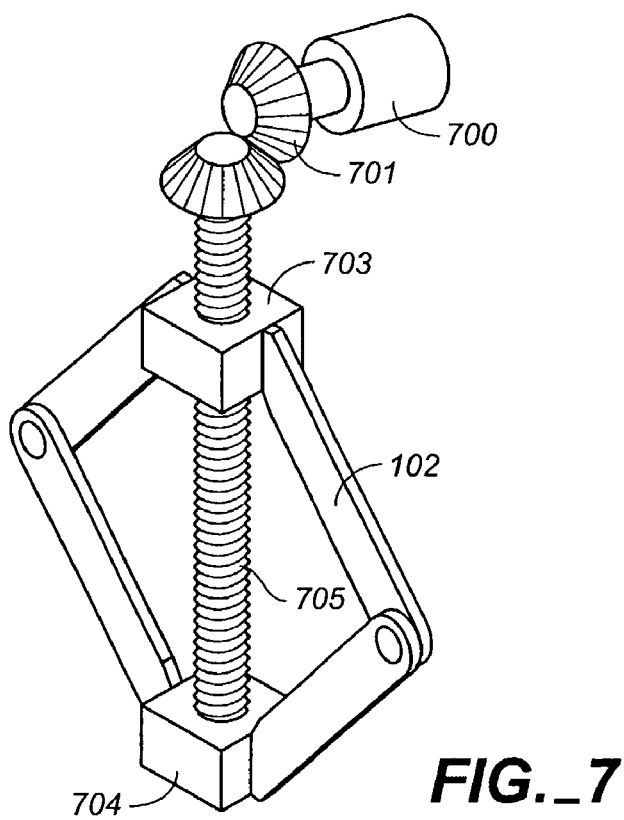
*FIG._7*
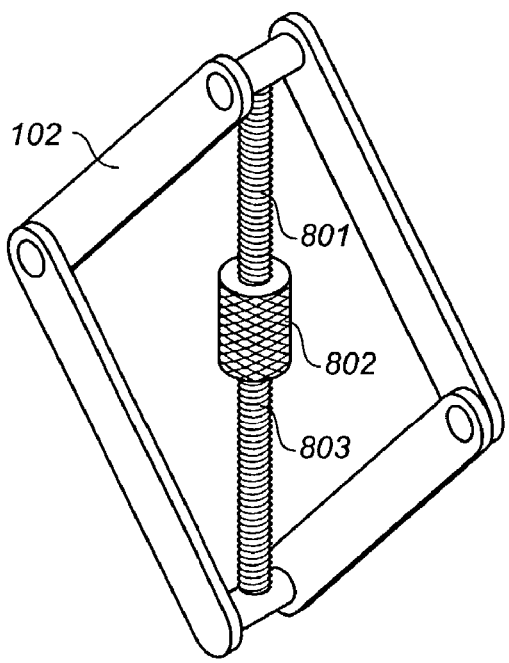
*FIG._8*

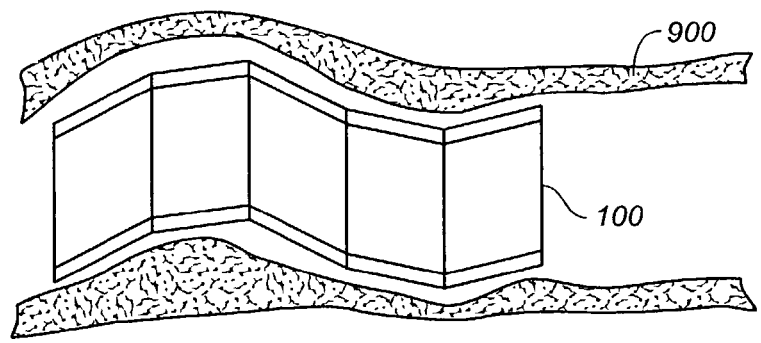
FIG._9
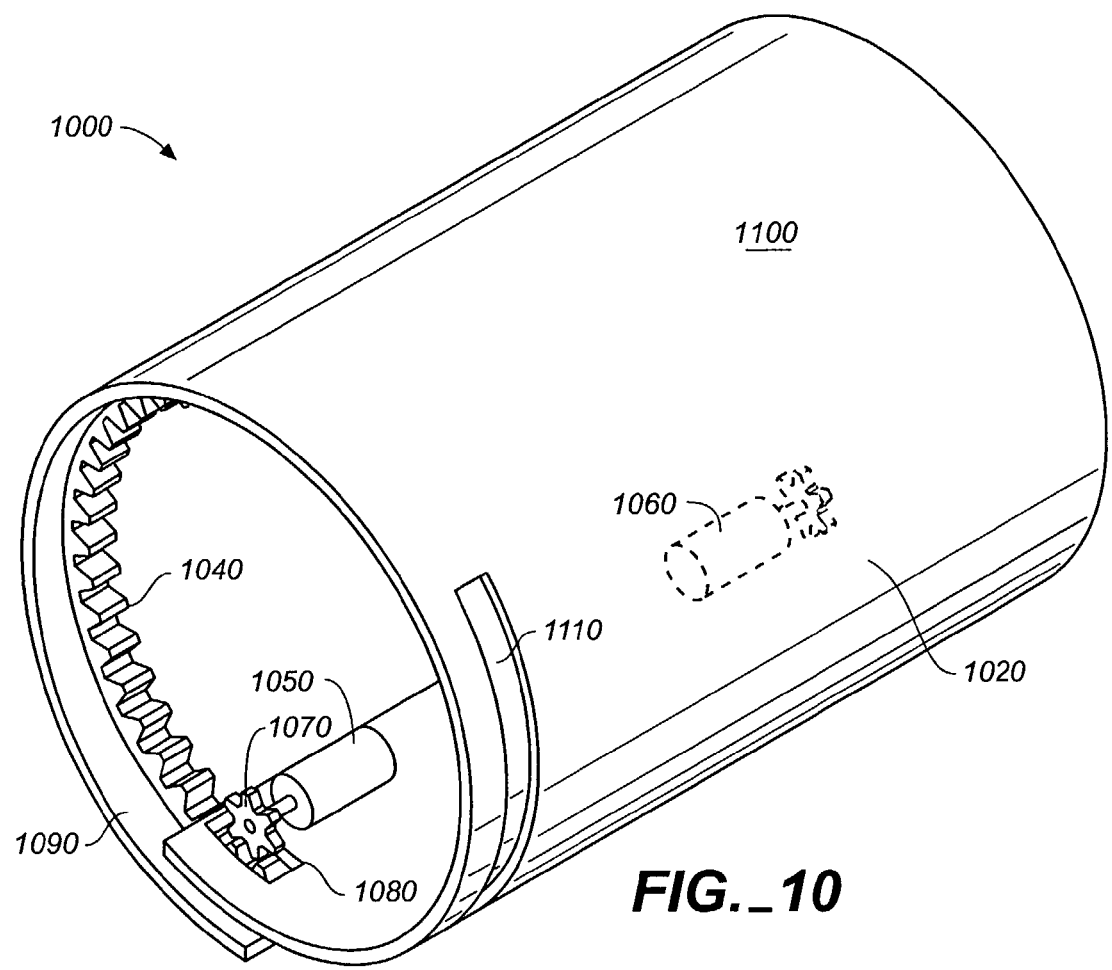
FIG._10

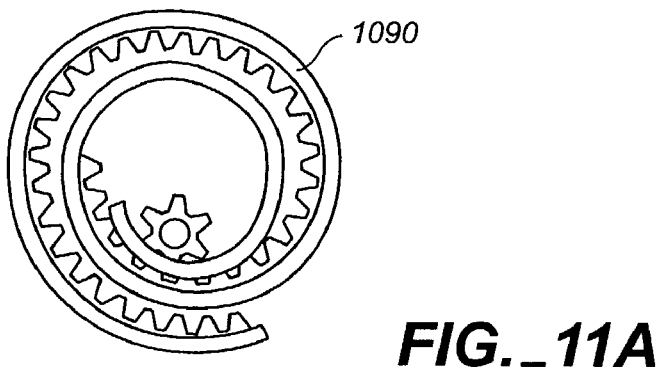
FIG._11A
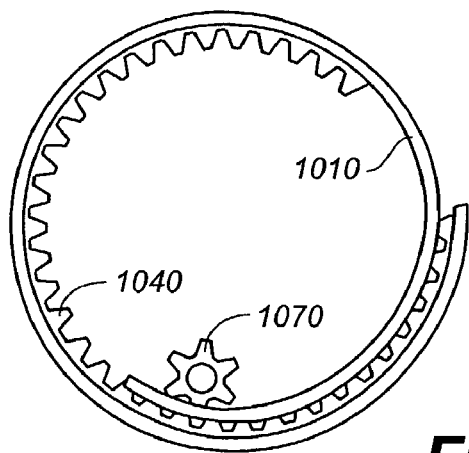
FIG._11B
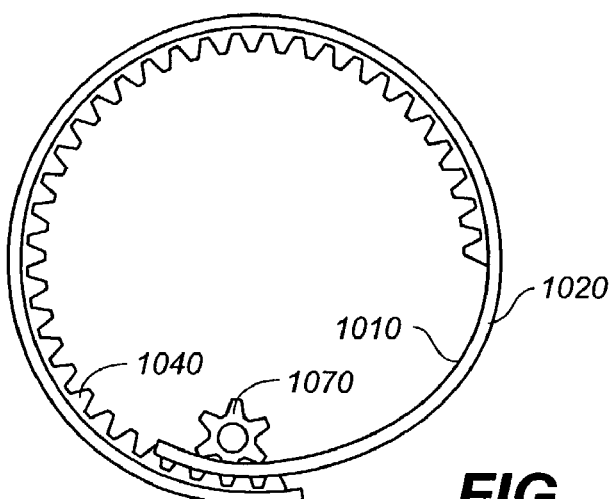
FIG._11C

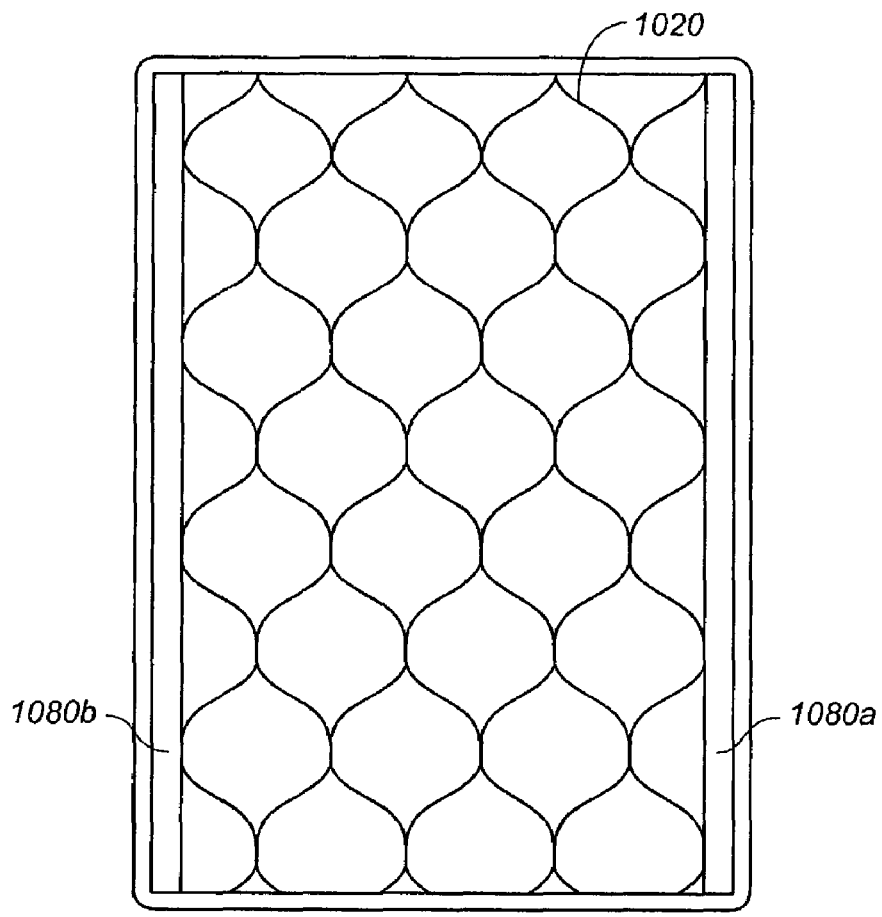
FIG._12
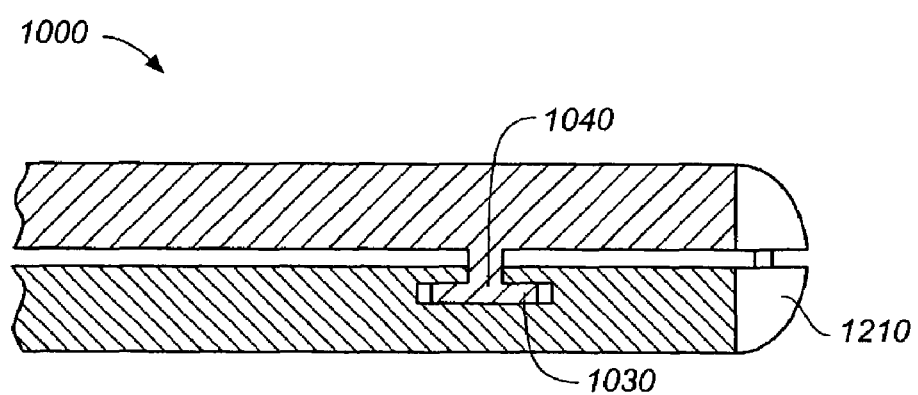
FIG._12A

FLEXIBLE MEMS ACTUATED CONTROLLED EXPANSION STENT

CROSS REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

TECHNICAL FIELD

The present invention relates generally to a medical device, and more particularly to a flexible, Micro-Electro-Mechanical Systems (MEMS) actuated, automatically controlled expansion stent for improving the vascular/arterial luminal diameter and prevention of restenosis.

BACKGROUND INFORMATION AND DISCUSSION OF RELATED ART

Coronary artery disease (CAD) is the leading cause of death among men and women in the United States, accounting for approximately one of every five deaths. Approximately 2.4 million adults have a history of myocardial infarction (MI), angina, or both, and it is estimated that millions of others have clinically silent coronary artery disease.

The traditional view has been that myocardial ischemia in CAD results from atherosclerotic plaques that narrow the vessel's lumen and decrease myocardial blood supply. However, research has shown that the reduction of blood flow results from the combination of fixed vessel narrowing and abnormal vascular tone, contributed to by atherosclerosis induced endothelial cell dysfunction.

Atherosclerotic coronary arteries can be treated by several methods. These treatment methods are divided into two major categories: non-invasive and invasive. Non-invasive treatments of coronary artery disease involve both medication and reduction of controllable risk factors of atherosclerosis. Non-invasive treatments cannot improve the coronary circulation when symptoms associated with coronary heart disease are severe. In such cases, invasive treatments are required to improve blood flow to the heart muscle. The most common invasive treatments for coronary heart disease include coronary artery bypass surgery (CABG), Percutaneous Transluminal Coronary Angioplasty (PTCA) and the use of percutaneously introduced prosthetic devices, namely, coronary stents. In CABG, a superfluous vein is removed from the patient's leg and sewn into the blood vessels that supply oxygenated blood to the heart. This transplanted vein, known as a graft, carries blood to the heart muscle, bypassing atherosclerotic areas in the coronary arteries. Alternatively, an internal mammary artery can be directly anastomosed distal to the stenotic site. CABG has become the most common major operation in the United States. It is usually a safe procedure with a ten-year patency rate of approximately 80–90 percent. Coronary bypass surgery effectively relieves chest pain (angina pectoris), increases exercise capacity, improves heart function in some patients, and prolongs life in certain patients. With current techniques, CABG requires a one-week hospitalization.

In PTCA, the lumen of an atherosclerotic coronary artery is increased by the inflation of an intravascular balloon catheter. Today, balloon angioplasty is used successfully to treat atherosclerosis in both systemic (peripheral, renal, cerebral) and coronary arteries in selected patients. The success rate of PTCA by an experienced staff ranges from 80 to 95 percent, and the average hospital stay after PTCA is roughly two days. Advantages of PTCA include decreased hospital stay, lower cost, decreased recuperation time, and no requirement of general anesthesia or chest incision. Although these advantages contributed to PTCA becoming a widely used alternative to coronary artery bypass surgery, the underlying mechanisms of balloon angioplasty continue to be elucidated. PTCA was originally thought to increase the lumen by compacting the atheromatous material within a relatively unyielding artery. Histological studies indicate, however, that the mechanisms of balloon angioplasty are much more complex and that the two primary mechanisms of this procedure are: (a) "over-stretching" of the vascular wall, which causes some mural injury, and (b) plaque fracture with partial separation from the vascular wall. This localized damage of the arterial wall is essential for a successful dilation via balloon angioplasty. Nevertheless, it is assumed that excessive damage likely contributes to complications such as restenosis, dissection, vasospasm, and rupture. Although this vascular wall damage results from mechanical forces, it is not known at which level of mechanical stress or strain it occurs.

The limitations of PTCA cited above resulted in the development of new technologies including atherectomy, laser angioplasty and coronary stenting.

The most significant change in interventional cardiology has been the growth of coronary stents, endovascular scaffolding devices that maintain the luminal integrity of diseased blood vessels. A typical stent implantation involves pre-dilatation of the target lesion via a PTCA procedure followed by implantation of the coronary stent in the same area of the coronary artery.

Clinical studies have shown that coronary stents improve the safety of PTCA by successfully treating abrupt and threatened closure, improve long-term clinical outcomes by reducing restenosis, and provide predictable angiographic results. Currently, coronary stents are available in several basic configurations: slotted tube, coil, mesh, ring, and multi-design. All are made of metal. Most stents are made of a plastically deformable material such as 316L stainless steel. Delivery of plastically deformable stents is commonly accomplished by the use of a balloon catheter. The balloon expandable stents are generally made of plastically deformable materials such as 316L stainless steel, elgiloy, nitinol, platinum-iridium and tantalum. They exhibit initial recoil due to elastic/plastic behavior of the plastically deformable stent material and initial vascular constriction. Once deployed, they provide fairly rigid scaffolding to the arterial lumen, thereby preventing abrupt closure and dissections. Self-expanding stents are generally secured on a delivery catheter under a constraining retractable sheath. Elgiloy and nitinol are the materials used for most self-expanding stent designs. Unlike the balloon expandable stents, which have some degree of recoil, self-expanding stents tend to continue expanding to their fixed diameters after deployment. Self-expanding stents do not expand beyond their pre-set nominal size. Therefore, pre-procedure proper sizing of the self-expanding stent is very important to prevent extensive vessel injury. It is not uncommon that both self-expanding and balloon expandable stents are post dilated to achieve optimum stent opposition. There are other stent designs such as bio-absorbable stents that are commonly manufactured using polymeric materials. They too are deployed using a balloon catheter. The primary advantages of such a stent over a metallic stent are: (a) there is a better match between stent stiffness and that of the vessel wall; and (b) they are designed to bio-absorb in the body after the diseased and injured vessel wall is healed. The disadvantages of such devices include low radial stiffness and visibility, and difficulty in identifying a biocompatible polymer for use in coronary arteries.

Clinically desirable stent characteristics include: minimal recoil; axial flexibility; low crossing profile; minimal surface area; adequate radial strength; good fluoroscopic visibility and good thrombo-resistance. Currently, none of the available stent designs incorporates all of these characteristics. Each stent design has its specific advantages and disadvantages. Acute clinical complications associated with coronary stenting include thrombosis (sub-acute), restenosis, bleeding due to required anticoagulation regimens, embolization, side-branch occlusion, coronary perforation and delivery balloon rupture.

Although several clinical studies have demonstrated that coronary stenting (when compared with PTCA alone) reduces restenosis rates in selected atherosclerotic lesions, restenosis within the stent (in-stent restenosis) remains a clinical problem. The incidence of in-stent restenosis has increased with recent advances in stent designs allowing stenting in difficult or less-than-ideal lesions, which leads to an intrinsically higher likelihood of restenosis following percutaneous intervention. It is estimated that of the 725,000 percutaneous coronary interventions completed in the United States, more than 80% will receive a new stent, and that 100,000 of these cases will develop symptoms due to in-stent restenosis.

The arteries, whose primary function is to carry blood from the heart to the capillaries, are generally subdivided into two categories. Those with large diameters and with many elastic constituents are called elastic arteries (e.g., aorta, carotids), whereas smaller diameter vessels are categorized as muscular arteries (e.g., coronaries, femorals). All arteries have similar wall organization and consist of three concentric layers.

The intima, or innermost layer of an artery, mainly consists of endothelial cells that line the vascular wall, the basement membrane, and a subendothelial layer. The subendothelial layer usually is present in large arteries with the exception of some special types of muscular arteries such as coronaries. The endothelial cells of the coronary arteries are elongated along the longitudinal axis of the vessel and constitute lineal folds. These endothelial folds of coronary arteries contribute to smooth peripheral blood flow and prevent the adherence of elements to the endothelial surface. The media, or middle layer of the artery, is composed of smooth muscle cells, a varied number of elastic sheets (laminae), bundles of collagen fibrils and a network of elastic fibrils all of which are embedded in a viscous gel matrix. The structure of the media is significantly different in elastic and muscular arteries. In elastic arteries, fenestrated elastic laminae, averaging 3 mm in thickness, are concentrically arranged and spaced equidistantly. Their numbers depend on the size of the elastic artery and vary between 20 and 60. A network of delicate elastic fibrils interconnects these elastic laminae. The smooth muscle cells are located within this framework. The majority of the smooth muscle cells are oriented obliquely, and run diagonally at small angles. The elastic components and the smooth muscle cells are held together by a network of collagen fibrils with two distinct and separate modes of fiber organization. The media of muscular arteries are distinguished by distinct internal elastic laminae separating the intima and the media, and less distinct external elastic laminae marking the outer border of the media. Compared to elastic arteries, muscular arteries do not have intermediate layers of concentric elastic laminae except in larger muscular vessels. Instead, muscular arteries consist of concentrically arranged populations of spindle-shaped smooth muscle cell layers. Concentrically arranged smooth muscle cells form helices that are invested within thin external lamina and narrow layers of delicate collagenous fibers. There is also a very fine network of elastin fibers throughout the media of the muscular arteries.

The adventitia, or the outermost layer of the arterial wall, consists primarily of longitudinally and circumferentially oriented collagen bundles, connective tissue cells, vasa vasorum, and a loose network of randomly oriented thin elastic fibers. Nerve cells and fibroblasts are also present in the adventitia. The thickness of the adventitia is not constant around the perimeter of the coronary arteries.

Arteries have been found to be thick-walled, nearly cylindrical, heterogeneous, anisotropic and nonlinearly viscoelastic composite materials. They undergo large deformations, relax when held at a constant strain, creep when subjected to a constant stress, and exhibit hysteresis when subjected to cyclic loading and unloading. Following preconditioning (i.e., sufficient number of loading cycles), their stress-strain relationship becomes unique, repeatable and predictable. In recent years in vivo studies performed on the coronary arteries to evaluate the role of coronary artery smooth muscle in the control of coronary circulation. These studies show not only a large potential contribution of coronary artery smooth muscle to arterial properties, but also the presence of a significant tone in coronary smooth muscle. The relative significance of this smooth muscle in the production of coronary spasm and in contributing to acute angina, however, remains unclear.

Biological tissues respond to mechanical stresses by growth and resorption when these stresses are applied over a long period of time. When the heart is overloaded its muscle cells increase in size. For example, the volume-overloaded heart increases its ventricular volume while a pressure-overloaded heart increases its wall thickness. When the oxygen supply to the lung is reduced suddenly, pulmonary blood pressure increases. As a result, the thickness of the adventitia and the smooth muscle layer in the pulmonary arteries increase, the lumens of small arteries decrease, and new muscle growth occurs on smaller and more peripheral arteries than normal. Pathological differences are observed (e.g., neointimal hyperplasia) in arteries stented via balloon-expandable versus self-expanding stents where slow growth of self-expanding stents yields greater late gains than those associated with the immediate large lumens achieved with balloon-expandable stents.

When shear stress due to blood flow artificially increases, histological and biochemical changes occur in the aortic endothelium. The transport of matter through cell membranes by active or passive mechanisms depends on strain in the cell membranes. Chemical reaction rate depends on pressure, stress, and strain. Therefore, it is reasonable to conclude that the remodeling of soft tissues involving growth and resorption of cells and extracellular materials is linked to the stress and strain in the tissue.

The determination of the failure characteristics of living tissues and organs is complex. There are many ways a material can fail in a biological sense. To study the failure characteristics of biological materials there must be correlative clinical observations and pathological examinations with stress and strain in the tissues. For example, soft tissues have very different stress-strain relationships than those of the typical engineering materials. Hysteresis, creep, and relaxation exist in soft tissues, and the strength of most soft tissues depends on the strain rate. In the physiological range, the stress in the soft tissue generally increases exponentially with increasing strain. At a certain strain higher than physiological, the tissue yields and breaks. Acute morphologic changes due to PTCA include endothelial denudation extrusion of fluid from the lesion, fracture of the plaque with partial separation from the underlying media, and "overstretching" of the vascular wall. The majority of the damage occurs in the intima and the inner half of the media, medial damage consists primarily of smooth muscle cell layer disruption including torn cell-to-cell and cell-to-elastin connections, the intimal and medial damage increases with increasing dilation, and the adventitia remains largely undamaged. Any mechanical trauma, which alters a tissue morphologically, also produces physiologic changes. In the case of balloon angioplasty, long term effects include platelet and fibrin deposition on the damaged endothelium, formation of neointima, removal of damaged myocytes by macrophages, edema, and synthesis of new collagen by fibroblasts. Physiologic changes also include differences in sodium pump activity, prostacyclin release, and changes in the artery's nutrient supply and metabolism. In summary, the general characteristics of arterial damage due to PTCA can be summarized as follows: intimal and medial damage, increasing with dilation; intramural damage greater in the inner wall than in the outer wall; longitudinal intimal-medial dissection; medial damage consisting primarily of disrupted smooth muscle, including torn cell-to-cell and cell-to-elastin connections and torn elastic (some collagen) fibers.

These findings are consistent with known stress distributions in non-uniformly inflated cylinders. That is, in addition to higher stress concentrations in the inner walls, shearing stresses are produced in the walls of the cylinder in the tangential-axial (EZ) and radial-axial (RZ) planes. Data on uniformly hyper-distended vessels further suggest that the smooth muscles (and basal lamina) probably tear first. Muscle tears more easily than connective tissue and is probably why muscle is often surrounded by protective connective tissue sheaths. Elastin appears to tear before collagen and is consistent with mechanical data. The modulus of elastin is orders of magnitude less than that of collagen, and elastin is less undulated than collagen. Thus elastin becomes taut well before the collagen. Because of this, it is a common misconception that a balloon exerts only a radial pressure on the intimal surface. Since vessels usually experience only normal stresses (except near branch sites), they are not designed to resist this type of load and may therefore be susceptible to shear induced tearing.

The primary obstacle to the long-term success of PTCA and coronary stenting is restenosis. The restenosis occurs within three to six months in 25–50% of patients who have PTCA and/or stenting procedures. Costly additional interventional or surgical procedures are usually required to treat the restenosis. It is well accepted that vascular restenosis or renarrowing of the lumen of the coronary artery is a direct response of the vessel injury incurred during revascularization. In a recent paper, it was stated that the common denominator for all current revascularization techniques appears to be vessel wall injury, independent of revascularization method (i.e., removal of vascular endothelium and exposure to deep tissue components).

Utilizing an animal model, Robert Schwartz showed that restenosis and the related neointimal response have a direct correlation to the amount of coronary artery injury, regardless of the intervention type. This observation is consistent with the restenosis rates reported in the literature for small vessel interventions. Although the same sizing criterion (balloon to reference vessel diameter) is used, the circumferential stretch ratio in the wall of small vessel would be higher than that of the larger diameter vessel, and thus, the amount of vascular injury in the small diameter vessel would be much higher. Similarly, the treatment of a long, diffused lesion with PTCA would require inconsistent "over-stretching" between the normal and diseased segments of the target vessel and thus result in increased vascular damage. There are several mechanisms that lead to restenosis: thrombosis; inflammation; smooth muscle cell migration/proliferation; and extra-cellular matrix formation/degradation. These represent the fundamental sequence of response to injury. The final clinical consequence of these mechanisms is late lumen renarrowing due to neointimal hyperplasia.

Historically, restenosis has been treated with medical therapy, balloon angioplasty, or CABG surgery. Specifically, if the original invasive procedure was angioplasty without stenting, the next step, once restenosis occurs, is usually to repeat the angioplasty followed by stent implantation. If restenosis occurs within a stent, it is usually treated by repeat angioplasty. However, once restenosis has occurred, the chance of a second restenosis nearly doubles.

Over the past decade, several new devices and strategies have been developed to reduce restenosis. These include directional, rotational and extractional atherectomy devices, excimer laser angioplasty and cutting balloon, but no therapy has consistently achieved reduction in restenosis. The focus of the prevention of restenosis has also been on the use of pharmacological agents. Local drug delivery devices, including drug-eluding stents, and even more sophisticated cell-based vascular gene-delivered systems have been developed. The clinical application and efficacy of such therapies, however, remains to be demonstrated.

Finally, the United States Food and Drug Administration (FDA) recently approved a new therapy, two catheter-based radiation therapies for the treatment of in-stent restenosis. However, the long-term safety of this novel therapeutic approach has been argued. There are associated problems such as edge restenosis, late thrombotic occlusions and potential delayed restenosis. In addition, incorporating intracoronary radiation in daily clinical practice has practical problems.

The nature of both PTCA and/or stenting (with predilatation) techniques is that they induce some degree of injury on the coronary artery wall via balloon dilatation. It is generally accepted that this so-called "controlled" wall injury is required to achieve the desired acute and long-term clinical outcomes. Inherent in response to this injury, restenosis remains to be a major clinical problem. Although, limiting the amount of injury during revascularization has been proposed as a means to limit the restenosis, there has been no attempt made to develop this idea further.

It would be desirable, therefore, to provide an interventional method that limits the amount of injury during revascularization and that comprises an alternative method to PTCA and current stenting practice. Such a revascularization technique would minimize vascular injury, and therefore, the restenosis rates associated with PTCA and stenting.

The vascular wall would not be injured (or the injury would be minimal) when it is stretched at an actively controlled manner (or strain rate) where stresses in the vascular wall remain at or below the physiologic levels at all times. Under such loading conditions, the vascular tissue including the endothelial layer would not be exposed to a major mechanical trauma. Instead, the vascular tissue would adapt (condition) or positively remodel in response to this actively controlled stretching. The remodeling would be different than the remodeling associated with the restenosis process (i.e., vascular response to injury—neointimal hyperplasia following PTCA). This device would provide adequate initial scaffolding upon deployment and allow actively controlled expansion (gradual or step-wise) of the vascular wall. The novelty of this method is that adequate flow through the diseased segments of blood vessels (or conduits) would be achieved by an actively controlled stent-like implantable device. Preferably, the device would be motorized (e.g., by Micro-Electro-Mechanical Systems, MEMS) or otherwise mechanically actuated to provide controlled, gradual or step-wise expansion of blood vessels. The controlled, gradual or step-wise expansion would prevent trauma to the tissue, thus eliminating potential long-term complications (such as restenosis), and allow blood vessels (the living tissue) to remodel in a controlled manner. The utility of this method is that, with MEMS and/or nano technology, it is possible to design and build such a state of the art interventional device.

BRIEF SUMMARY OF THE INVENTION

The present invention provides a medical device that includes structure and active motorized control mechanisms that are adapted to minimize vascular tissue damage and restenosis associated with traditional stenting techniques. The medical device includes structure that provides adequate initial scaffolding upon deployment and allows actively controlled expansion of the stent during deployment and over the lifetime of the medical device through a multiplicity of intermediate diameters to a fixed maximum diameter. For longer devices, the device will allow tapering of its diameter from proximal to distal end.

In a preferred embodiment, the medical device embodies a stent that has a generally overall tubular configuration. The stent body is defined by a plurality of radial expansion trusses connected longitudinally by a plurality of interconnects that repeat around the circumference of the expansion trusses, giving longitudinal rigidity and providing the tubular scaffolding of the device. The inner and outer surfaces of the tubular scaffolding are coated or covered with a thin film shape memory alloy, polymeric film, or other expansible material.

The expansion trusses are characterized by a plurality of hinged links that allow expansion or contraction of the radial expansion trusses in a synchronized manner, while maintaining the overall circular geometry of the radial expansion truss. The interconnects are fastened to the radial expansion trusses by a ball and socket type assembly. Energy is applied to specific links on the radial expansion truss, resulting in expansion of the device. Expansion of the radial expansion trusses is achieved by action of at least one Micro Electro Mechanical System (MEMS) motor on the radial expansion trusses. The MEMS motors apply force to a pull wire or lead screw which is fastened to selected links in the radial expansion trusses. Preferably, at least one load cell or pressure sensor is employed to detect forces applied to the vascular tissues, either directed by detecting pressure on the stent body, or indirectly by detecting resistance to the pull on the pull wires. The sensors feed the pressure information to a microprocessor, miniature PLC, or other control logic which controls the MEMS and thus the force imparted to the pull wire or lead screw by the MEMS. No balloon catheter is required to deliver, expand or deploy the device.

In another preferred embodiment of the medical device, a stent is formed by a shape memory or any metallic alloy is coiled into a generally tubular shape. Expansion of the coiled shape memory or any metallic alloy (with pre-cut expandable slots) is actively controlled by the use of at least one MEMS motor attached to the interior terminal edge of the coiled shape memory or any metallic alloy, in a rack and pinion gear assembly. The MEMS motor employs a pinion gear mounted on a shaft. The gear protrudes through a slot in the shape memory or any metallic alloy, connecting with a raised gear rack which is attached to the inner surface of the shape memory or any metallic alloy in a linear manner centered on the same radial line as the pinion gear and the associated slot. A cross section of the track will assume a general shape having a lower portion of a smaller cross sectional dimension than the upper portion containing the track surface. The top surface of the track is of a reciprocal shape to the pinion gear employed by the MEMS motor, providing a positive traction surface for radial expansion of the stent. The lower section of the gear rack serves as the attachment point to the shape memory or any metallic alloy.

The exterior surface of the coiled shape memory or any metallic alloy employs a groove exactly opposite the gear rack on the interior surface of the shape memory alloy coiled material. The groove is of a reciprocal shape to the rack, which allows insertion of the rack into the groove when the shape memory or any metallic alloy is in the coiled state, and allows the rack to slide in the groove. The reciprocal shape of the groove prevents the rack from sliding out of the grove and maintains the overall tubular structure of the stent. The MEMS motor and gear assembly act to provide a mechanism to uncoil the shape memory or any metallic alloy, thus achieving radial expansion in a controlled manner. At least one pressure sensor is employed to detect forces applied to the vascular tissues. The sensor feeds the pressure information to a microchip which controls the force imparted to the gear by the MEMS motor.

BRIEF DESCRIPTION OF THE SEVERAL VIEWS OF THE DRAWINGS

FIG. 1 is a perspective view of a first preferred embodiment of the flexible MEM actuated controlled expansion stent of the present invention;

FIG. 1A is a perspective view of the medical device of the FIG. 1 in a fully collapsed configuration;

FIG. 1B is a perspective view of the medical device of FIG. 1 in a partly expanded configuration;

FIG. 1C is a perspective view of the medical device of FIG. 1 in a fully expanded configuration;

FIG. 2A is a schematic end view of a radial expansion truss corresponding to FIG. 1A;

FIG. 2B is an end view schematic representation of the radial expansion truss corresponding to FIG. 1B;

FIG. 2C is an end view schematic representation of the radial expansion truss corresponding to FIG. 1C;

FIG. 3 is a perspective view schematic representation of the radial expansion truss of FIG. 1 depicting a series of paddle-shaped interconnects operatively connected to a radial expansion truss and a series pull wires extending through and from the interconnects actuated to achieve expansion of the radial expansion truss connected to the radial expansion truss through the interconnects;

FIG. 4 is a schematic cross-sectional side view in elevation of a preferred embodiment of the medical device in FIG. 1, depicting a series of three radial expansion trusses with a transverse sectional view of a MEMS motor, transverse sectional view of the interconnects and a depiction of the path of the pull wires;

FIG. 4A is a schematic cross-sectional side view in elevation showing detail of the interconnect and truss attachment;

FIG. 4B is an end view of the ball joint of an interconnect;

FIG. 5 is a schematic representation of an angled link of the radial expansion truss of FIGS. 1A through 2C, showing detail of the socket joint for operative connection to a ball joint of an interconnect;

FIG. 6 is a schematic cross-sectional side view in elevation of an alternative embodiment of the present invention shown in FIG. 1, depicting a series of three radial expansion trusses, each having a dedicated MEMS motor to urge the radial expansion truss into expansion;

FIG. 7 is a perspective view of a third preferred embodiment of the present invention, in which the links of a radial expansion truss employ a MEMS motor mounted on the link, driving a lead screw to achieve expansion of the radial expansion truss;

FIG. 8 is a schematic representation of a fourth preferred embodiment of the medical device of the present invention showing that the links of a radial expansion truss may employ a MEMS motor mounted between two lead screws to achieve expansion of the radial expansion truss through a turnbuckle assembly;

FIG. 9 is a side view representation of the medical device of FIG. 1 deployed in a coronary artery, showing that the stent permits pivotal movement of the ball and socket assembly of the connection between interconnects and expansion truss links so as to facilitate flexibility in the stent;

FIG. 10 is a perspective view of a fifth preferred embodiment of the medical device of the present invention, depicting a coiled shape memory or any metallic alloy utilizing a MEMS motor to control radial expansion;

FIG. 11A is a schematic diagram cross sectional end view of the medical device of FIG. 10 in a fully coiled state;

FIG. 11B is a schematic diagram cross sectional view of the medical device of FIG. 10 in a partially expanded state;

FIG. 11C is a schematic diagram cross sectional view of the medical device of FIG. 10 in a fully expanded state;

FIG. 12A is a is a schematic diagram transverse sectional view of the medical device of FIG. 10 in the fully coiled state; and FIG. 12B is a detailed cross-sectional side view in elevation of the gear mechanism of the apparatus of FIGS. 10–12.

DETAILED DESCRIPTION OF THE INVENTION

Referring to FIGS. 1 through 12, wherein like reference numerals refer to like components in the various views, FIG. 1 is a perspective view of the flexible MEM actuated controlled expansion stent of the present invention. The stent generally comprises a tubular body embodying structure that allows controlled radial expansion when the stent is deployed into vasculature. Specifically, the medical device includes physical and operational structure that enables it to be radially expanded in a controlled manner by the use of MEMS technology, providing optimal control of the expansion rate (gradual or step-wise) of the medical device and utilizing pressure or force sensors to evaluate the pressures/forces exerted on the vascular wall by the expansion, thus reducing injury to vascular tissue that lead to restenosis.

In its first preferred embodiment, the medical device of the present invention comprises a stent 100 having a stent body 101. The stent body is generally tubular in shape and includes a plurality of radial expansion trusses 102 that share a common longitudinal axis 106. The radial expansion trusses are connected to one another by a plurality of interconnects 103. The interconnects can be arranged at spaced intervals longitudinally along the circumference of the stent body 101. The size of the intervals may be even or uneven, though truss structure will ordinarily entail a substantially even spacing. A plurality of MEMS motors 104 are connected to the terminal ends of the most distal 103a and most proximal 103b interconnects 103. MEMS suitable for use or easily adapted for use in the inventive stent are commercially available. MicroMo Electronics, Inc., of Clearwater, Fla., offers a 0206 series micro motor and 02/1 micro planetary gearbox having outer diameters of only 1.9 mm. The system was developed by the Faulhaber Group of Companies in cooperation with the Institut für Mikrotechnik Mainz. Smaller systems have been described in early literature, including those discussed in "IC-Processed Electrostatic Synchronous Micromotors," Sensors and Actuators, Vol. 20, No. 1–2, Nov. 15, 1989, pp. 49–55, by Y. C. Tai and R. S. Muller.

A thin film shape memory alloy or polymer 105 covers the exterior of the stent body 101. The interior of the stent is also preferably covered with a shape memory, polymer, or other metallic alloy layer 107, thus effectively sandwiching the expansion trusses and interconnects between two thin expansible layers.

Referring now to FIGS. 1A through 1C, in FIG. 1A the stent 100 is shown in perspective view in a fully collapsed configuration, in a partially expanded configuration in FIG. 1B, and in a fully expanded configuration in FIG. 1C. Included in FIGS. 1A through 1C are components of the radial expansion truss 102, which comprises a plurality of triangular shaped links 110, angulated links 111, and notched angulated links 112, attached by hinged pivot points 114. Also depicted is the interconnect 103 attachment point 113 to the radial expansion truss 102. Referring now to FIGS. 2A through 2C, the radial expansion truss 102 is depicted in an end view in a fully collapsed configuration in FIG. 2A, in a partially expanded configuration in FIG. 2B, and in a fully expanded configuration in FIG. 2C.

With reference to FIG. 3, the radial expansion truss 102 is shown in perspective view as having a plurality of arcuate, or paddle-shaped interconnects 103, each having an interconnect ball joint 302 and shaft 304 at the distal and proximal ends of the interconnect. The interconnect attaches to the radial expansion truss 102 at a socket-shaped pivot point 303 on the radial expansion truss. A pull wire 304 exits the interconnect 301 and attaches to the radial expansion truss 102 by a weld 305. As force is exerted on the pull wire 304 by a MEMS motor, the radial expansion truss 102 is expanded.

FIGS. 4 and 4A are schematic cross-sectional side views in elevation showing a transverse section of two interconnects 103 and their attachments to radial expansion trusses 102. A detail of the interconnect depicts a longitudinal channel 320 running the length of the interconnect 103, through which a plurality of pull wires 304 may be passed. Also shown is a perpendicular channel 321 through the interconnect ball joint 302. This channel 321 allows a pull wire 304 to be passed down the radius of the radial expansion truss 102 to an attachment point 305. The MEMS motor 104 is depicted in transverse section. The MEMS motor 104 contains a power supply 312 connected to a drive mechanism 311 which in turn rotates a reduction gear 310 which acts upon a spool 315 that imparts force upon the pull wire 304. The MEMS motor provides the force to expand the radial expansion truss 102. In this preferred embodiment, one MEMS motor 104 may control the expansion of a plurality of radial expansion trusses 102.

The stent also preferably includes pressure sensors or load cells 316. The sensors feed the pressure information from the pull wires, reduction gears, or truss members to a microprocessor, miniature PLC, or other control logic 318 which controls the MEMS and thus the force imparted to the pull wire or lead screw by the MEMS. The motor control may be incorporated into each motor so that each motor activates and responds independently of the other motors, or a single control logic device may be physically incorporated into the stent and coupled to a plurality of pressure sensors. In yet another alternative, the logic device may be kept external to the body and connected to bundled trace wires from the sensors. In this fashion, operation of the stent may be monitored and controlled by the treating physicians as well as automatically by control algorithms.

FIG. 4B shows that the arc α 322 described by each interconnect is such that in the entirely collapsed configuration, the interconnects abut one another edge to edge. Accordingly, for example, in an apparatus having nine interconnects joining each expansion truss, the arc described by each interconnect would be 40°; in a stent having twelve interconnects, the arc described by each interconnect would be 30°, and so forth.

FIG. 5 shows an angulated link 111 with detail of a cupped socket 500 fashioned to accept the interconnect ball joint 302, and a slot 501 to accommodate a pull wire 304, passed through the perpendicular channel 321. The slot 501 is fashioned to accommodate a multiplicity of angles that may be assumed by the pull wire 304 during expansion of the stent 100 from FIG. 1.

FIG. 6 is a schematic view of a second preferred embodiment of an expansion mechanism for the stent 100 of FIG. 1. Three MEMS motors 104 are connected to individual radial expansion trusses 102 to achieve expansion.

FIG. 7 depicts a third preferred embodiment of the stent 100 from FIG. 1, wherein a MEMS motor 700 turns a beveled drive gear 701 which meshes with a beveled screw gear 702, each gear with intersecting axes, to turn a screw 705. The lead screw 705 is passed through a threaded nut 703 at the external circumference of the radial expansion truss and attached to a base 714 at the internal circumference if the radial expansion truss 102. The base 714 allows the screw 704 to rotate, thus initiating expansion of the radial expansion truss 102.

FIG. 8 is a fourth preferred embodiment of the stent 100 from FIG. 1. In this embodiment, expansion of the radial expansion truss 102 is achieved by a MEMS motor 802 positioned equidistant between a right handed screw 801 connected to the outer circumference of the radial expansion truss 102 and a left handed screw 803 connected to the inner circumference of the radial expansion truss 102. The MEMS motor 802 turns and pulls the right handed screw 801 and the left handed screw 803 together to achieve expansion of the radial expansion truss 102.

FIG. 9 is a graphic depiction of the stent 100 of FIG. 1 placed in a coronary artery 900. This depiction shows the ability of the stent 100 of FIG. 1 to conform to the shape of the coronary artery 900.

FIG. 10 is a perspective view of a fourth preferred embodiment of a coiled controlled expansion stent 1000, and FIG. 11A is a cross sectional end view thereof, shown in the fully coiled state. FIG. 11B shows a partially expanded configuration and FIG. 11C shows a fully expanded state. In this embodiment, the stent body comprises a coiled shape memory alloy or any metallic alloy that has a shape much like that of an elongated flat coiled spring. The stent body 1020 includes pre-cut slots 1080a, 1080b, and the overlapping portion of the body is uncoiled actively through the use of at least one MEMS motor 1050, 1060 having a pinion gear 1070 in mesh with a rack gear 1040 attached proximate the interior terminal edge 1090 of the coiled shape memory or any metallic alloy and attached to the inner surface 1010 of the shape memory or any metallic alloy in a linear manner centered on the same radial line as the pinion gear and the associated slot. The track has a lower portion attached to the stent body and has a smaller cross sectional dimension than the upper portion containing the track surface. The top surface of the track is of a shape complementary to the pinion gear employed by the MEMS motor, providing a positive traction surface for radial expansion of the stent.

The exterior surface 1100 of the coiled shape memory or any metallic alloy employs a groove 1110 opposing the gear rack on the interior surface of the shape memory alloy coiled material. The groove is of a reciprocal shape to the rack, allowing insertion of the rack into the groove when the shape memory or any metallic alloy is in the coiled state, and allowing the rack to slide in the groove during expansion. The reciprocal shape of the groove also prevents the gear rack from sliding out of the grove and maintains the overall tubular structure of the stent.

As in the first preferred embodiment, preferably at least one pressure sensor is employed to detect forces applied to the vascular tissues. The sensor feeds the pressure information to a microchip or other logic which controls the force imparted to the gear by the MEMS motor.

FIG. 12A is a is a schematic diagram transverse sectional view of the medical device of FIG. 10 in the fully coiled state. This view does not show the motors but illustrates, instead, the open mesh characteristic of the stent body and the geometry of the expansible grooves 1080a/b. FIG. 12B is a detailed cross-sectional side view in elevation of the gear mechanism of the apparatus of FIGS. 10–12.

In each of the preferred embodiments, power for the MEMS and the pressure sensors may be provided by cells or batteries (not shown) incorporated into the stent body or into the MEMS and sensors themselves, or by an external electrical power source connected to the MEMS and sensors by a trace wire. Alternative approaches to the provision of electrical power to the system components will be evident to those with skill in the art.

As will be readily appreciated, in its most essential aspect the inventive apparatus comprises an automatically controlled expansion stent having an expansible stent body, actuation means for expanding the stent body, and control means for actively controlling the actuation means. More specifically, the inventive stent is a substantially tubular stent body that comprises material layers covering a plurality of radial expansion trusses, and employs MEMS motors under the control of a programmable logic device to expand the trusses, and thus the stent body. Force from the motor is communicated to the expansion trusses through interconnects, which pivotally connect the trusses and provide channels for pull wires extending from the motors to the trusses. The trusses comprise a plurality of hinged links which provide symmetrical expansion of the stent body.

The inventive device thus provides an improved method of reducing restenosis in vascular tissue when employing a percutaneously introduced prosthetic device, the method comprising the steps of: (a) providing an automatically controlled expansion stent having an expansible stent body, actuation means for expanding the stent body; (b) providing programmable control means for actively controlling the actuation means; (c) programming the programmable control means to expand the stent body at a predetermined rate and to a predetermined maximum diameter; and (d) deploying the stent into a patient's body using conventional stenting techniques. The steps will almost invariably take place in the above-indicated order, though it will be readily appreciated that programming may precede incorporation into the stent, may take place after installation into the stent, or may, in some instances, take place after deployment in cases where electrical communication is maintained with the stent after deployment.

While the present invention has been shown in the drawings and fully described above with particularity and detail in connection with what is presently deemed to be the most practical and preferred embodiment(s) of the invention, it will be apparent to those of ordinary skill in the art that many modifications thereof may be made without departing from the principles and concepts set forth herein, including, but not limited to, variations in size, materials, shape, form, function and manner of operation, assembly and use.

Accordingly, the proper scope of the present invention should be determined only by the broadest interpretation of the appended claims so as to encompass all such modifications as well as all relationships equivalent to those illustrated in the drawings and described in the specification.

What is claimed as invention is:

1. An automatically controlled expansion stent, comprising:
    a substantially tubular expansible stent body comprising a first and a second end, inner and outer wall surfaces, and a first diameter that permits intraluminal delivery;
    at least two radial expansion trusses for expanding said stent body, said expansion trusses composed of a plurality of hinged links which allow symmetrical expansion of the radial expansion trusses, and further including a plurality of interconnects interposed between said radial expansion trusses;
    actuation means for selectively expanding said stent body mechanically, wherein the expansion of said stent body does not involve a plastic deformation process or utilize shape memory material characteristics;
    control means for actively controlling said actuation means;
    wherein said hinged links comprise a combination of triangular shaped links, angulated links, and notched angulated links, each attached to an adjoining link by hinged pivot points.

2. The stent of claim 1, wherein said interconnects are arcuate, and wherein said interconnects form a closed cylindrical body when said stem is in a collapsed configuration and are evenly spaced apart when said stent is in a partially expanded or fully expanded configuration.

3. The stent of claim 2, wherein said interconnects each have an interconnect ball joint and shaft at each end and attaches to said radial expansion truss at a socket-shaped pivot point on the radial expansion truss.

4. An automatically controlled expansion stent, comprising:
    an expansible stent body;
    at least one Micro-Electro-Mechanical-System (MEMS) motor operatively connected to said stent body for selectively expanding said stent body mechanically, wherein the expansion of said stent body does not involve a plastic deformation process or utilize shape memory material characteristics; and
    control means for actively controlling said MEMS motor, wherein said control means is electrically connected to said MEMS motors and comprises a device selected from the group consisting of a PLC and a microprocessor.

5. An automatically controlled expansion stent, comprising:
    an expansible substantially tubular stent body having first and second ends, inner and outer wall surfaces, and a first diameter that permits intraluminal delivery;
    at least one Micro-Electro-Mechanical-System (MEMS) motor operatively connected to said stent body for expanding said stent body;
    control means for actively controlling said MEMS motor;
    wherein said tubular body is enlarged by the use of at least two radial expansion trusses composed of a plurality of hinged links which allow symmetrical expansion of the radial expansion trusses, and further including a plurality of interconnects interposed between said radial expansion trusses; and
    wherein each of said MEMS motors is connected to at least one radial expansion truss through a pull wire extending through at least one of said interconnects which attaches to said radial expansion truss, and wherein as force is exerted on said pull wire by said MEMS motor, said radial expansion truss is expanded.

* * * * *